United States Patent
Suzuki et al.

(10) Patent No.: US 9,207,202 B2
(45) Date of Patent: Dec. 8, 2015

(54) GAS SENSOR ELEMENT, GAS SENSOR EQUIPPED WITH GAS SENSOR ELEMENT, AND METHOD OF PRODUCING GAS SENSOR ELEMENT

(75) Inventors: Yasufumi Suzuki, Kariya (JP); Masatoshi Ikeda, Aichi-ken (JP)

(73) Assignees: DENSO CORPORATION, Kariya (JP); NIPPON SOKEN, INC., Nishio (JP)

( * ) Notice: Subject to any disclaimer, the term of this patent is extended or adjusted under 35 U.S.C. 154(b) by 609 days.

(21) Appl. No.: 12/765,994

(22) Filed: Apr. 23, 2010

(65) Prior Publication Data
US 2010/0270155 A1    Oct. 28, 2010

(30) Foreign Application Priority Data
Apr. 23, 2009  (JP) .................. 2009-105009

(51) Int. Cl.
*G01N 27/407*    (2006.01)

(52) U.S. Cl.
CPC .................. *G01N 27/4075* (2013.01)

(58) Field of Classification Search
CPC ................................................ G01N 27/4075
USPC ........................................................ 204/429
See application file for complete search history.

(56) References Cited

U.S. PATENT DOCUMENTS

| 6,667,018 B2 * | 12/2003 | Noda et al. ................. 423/213.5 |
| 2007/0144905 A1 * | 6/2007 | Tsuji et al. ..................... 204/424 |
| 2007/0151851 A1 | 7/2007 | Tanaka et al. |

FOREIGN PATENT DOCUMENTS

| JP | 61-045962 | 3/1986 |
| JP | 2007-199046 | 8/2007 |
| JP | 2007-206055 | 8/2007 |

OTHER PUBLICATIONS

Japanese Office Action dated Apr. 19, 2011 issued in corresponding Japanese Application No. 2009-105009 with English Translation.

* cited by examiner

*Primary Examiner* — Luan Van
*Assistant Examiner* — Louis Rufo
(74) *Attorney, Agent, or Firm* — Nixon & Vanderhye P.C.

(57) ABSTRACT

A gas sensor element has a solid electrolyte of an oxygen ion conductivity, a target gas electrode formed on one surface of the solid electrolyte, a reference gas electrode formed on the other surface of the solid electrolyte, a porous diffusion resistance layer through which the target gas passes to reach the target gas electrode, and a catalyst layer formed on an outer surface of the porous diffusion resistance layer. The target gas electrode is formed around the porous diffusion resistance layer. The catalyst layer contains noble metal catalysts. The noble metal catalysts contain at least rhodium and palladium. A content of rhodium is not less than 10 mass % and a content of palladium is not less than 20 mass % to the entire of the noble metal catalysts.

11 Claims, 6 Drawing Sheets

GAS SENSOR ELEMENT, GAS SENSOR EQUIPPED WITH GAS SENSOR ELEMENT, AND METHOD OF PRODUCING GAS SENSOR ELEMENT

CROSS-REFERENCE TO RELATED APPLICATION

This application is related to and claims priority from Japanese Patent Application No. 2009-105009 filed on Apr. 23, 2009, the contents of which are hereby incorporated by reference.

BACKGROUND OF THE INVENTION

1. Field of the Invention

The present invention relates to gas sensor elements, gas sensors equipped with the gas sensor element therein capable of detecting a concentration of a specific gas contained in a target gas, and a method of producing the gas sensor element.

2. Description of the Related Art

There are various types of gas sensor elements which are widely known and used.

Figure 5:
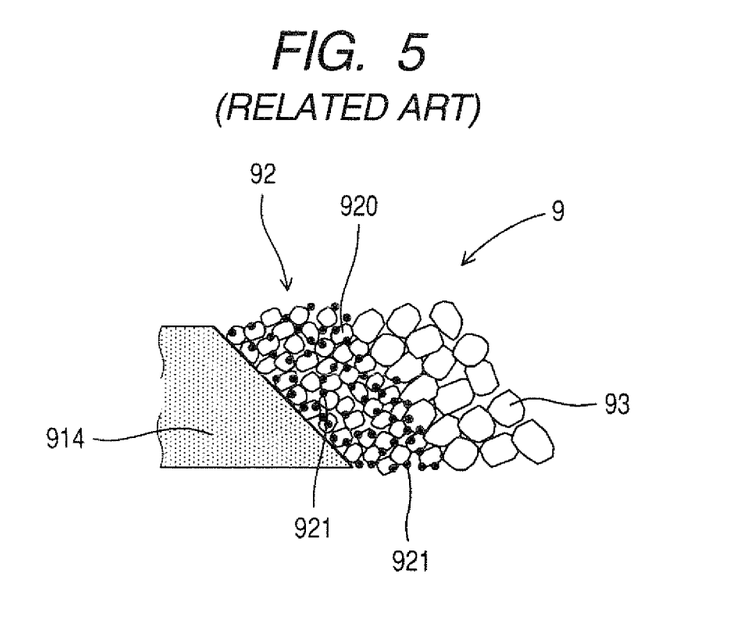
FIG. 5 is a cross section showing a catalyst layer in a conventional gas sensor element.
Figure 6A:
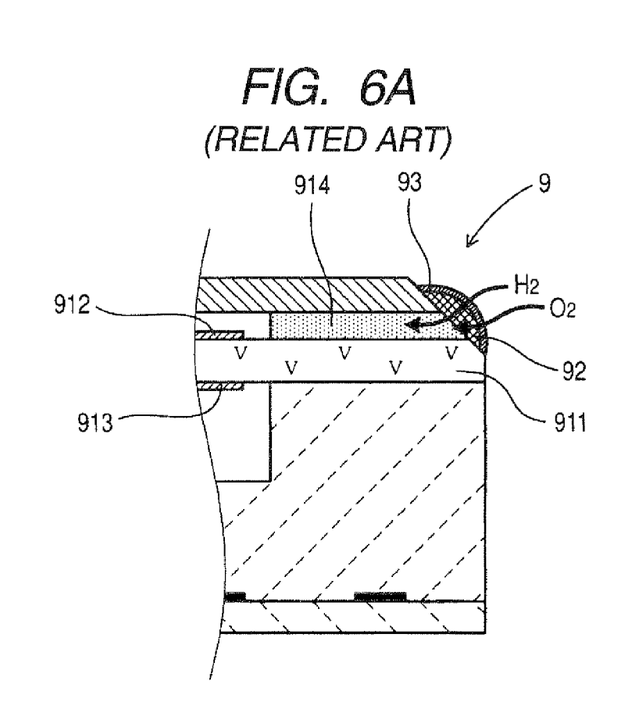
FIG. 6A is a view to explain a state where a target gas is passing through a trap layer and the catalyst layer in the conventional gas sensor element.
Figure 6B:
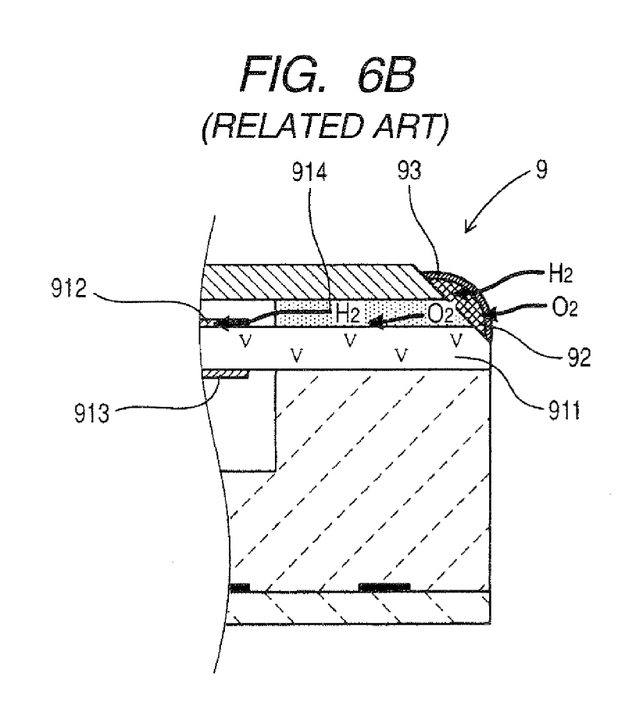
FIG. 6B is a view to explain a state where the target gas reaches a target gas electrode in a target gas chamber in the conventional gas sensor element.

FIG. 5 is a cross section showing a catalyst layer in such a conventional gas sensor element. FIG. 6A is a view to explain a state where a target gas is passing through a trap layer and the catalyst layer in the conventional gas sensor element 9. FIG. 6B is a view to explain a state where the target gas reaches a target gas chamber 940 in the conventional gas sensor element.

For example, as shown in FIG. 5, FIG. 6A, and FIG. 6B, one type of those conventional gas sensor element is comprised of a solid electrolyte 911, a target gas electrode 912, a reference gas electrode 913, a porous diffusion resistance layer 914, and a catalyst layer 92. The solid electrolyte 911 has a oxygen ion conductivity. The target gas electrode 912 is formed on one surface of the solid electrolyte 911. The reference gas electrode 913 is formed on the other surface of the solid electrolyte 911. As shown in FIG. 6A and FIG. 6B, the porous diffusion resistance layer 914 surrounds the target gas electrode 912. The target gas to be detected passes through the porous diffusion resistance layer 914, and reaches the target gas electrode 912. The catalyst layer 92 is formed at the outer surface of the porous diffusion resistance layer 914 through which the target gas is introduced into the inside of the gas sensor element 9. The catalyst layer 92 contains noble metal catalyst 921.

The target gas contains CO gas, NO gas, and $H_2$ gas. Combustion of $H_2$ gas is performed in the catalyst layer 92 formed in the gas sensor element 9. When the gas sensor element 9 has no catalyst layer, $H_2$ gas is not burned and reaches the target gas electrode 912 in the target gas chamber 940 at high speed rather than $O_2$ gas. This makes it for the gas sensor element 9 to output an incorrect detection signal which is away from a true detection signal regarding a concentration of a specific gas contained in the target gas because $H_2$ gas has a light molecular weight and is capable of being rapidly passing through the inside of the porous diffusion resistance layer 914 when compared with other gases such as $O_2$ gas.

Further, for example, there is a tendency to increase the amount of $H_2$ gas in an exhaust gas emitted from a direct injection engine in addition when the engine starts to work because of having a different combustion mechanism.

Still further, there is a tendency to increase the amount of $H_2$ gas in an exhaust gas emitted from CNG (compressed natural gas) engines because of having different fuel composition when compared with that of the gasoline engines.

Therefore those engines have a problem where the gas sensor element outputs an incorrect detection signal which is different from a true detection signal regarding the concentration of a specific gas contained in a target gas because $H_2$ gas passes at a high speed in the porous diffusion layer compared to other gases.

In order to solve the above conventional problem, as shown in FIG. 5, conventional techniques have proposed the gas sensor element 9 having the catalyst layer 92 formed on the outer surface of the porous diffusion resistance layer 914. The catalyst layer 92 contains platinum and palladium, in particular, contains 2 to 56 mass % of palladium in the entire noble metal catalyst 921. For example, Japanese patent laid open publication No. JP 2007-199046 discloses such a conventional gas sensor element capable of preventing an incorrect detection which is away from a true detection value.

However, this conventional gas sensor element 9 disclosed in JP 2007-199046 has the following problem. That is, this conventional gas sensor element can prevent occurrence of an incorrect detection result which is away from its true detection value of the target gas, but, there is a probability of deteriorating the noble metal catalyst 921 in the catalyst layer 92.

Therefore there is a strong demand to provide an improved gas sensor element capable of preventing outputting an incorrect detection signal which is away from a true detection signal and also preventing deterioration of the catalyst layer in the gas sensor element.

SUMMARY OF THE INVENTION

It is an object of the present invention to provide a gas sensor element having a catalyst layer with high durability, which is capable of preventing occurrence of outputting an incorrect detection signal which is away from a true output.

In accordance with a first aspect of the present invention, there is provided a gas sensor element having a solid electrolyte of an oxygen ion conductivity, a target gas electrode formed on one surface of the solid electrolyte, a reference gas electrode formed on the other surface of the solid electrolyte, a porous diffusion resistance layer capable of permeating the target gas and surrounding the target gas electrode, and a catalyst layer. This catalyst layer is formed on an outer surface of the porous diffusion resistance layer. Through the catalyst layer, the target gas is introduced into the inside of the gas sensor element. In particular, the catalyst layer contains noble metal catalysts. The noble metal catalyst contain at least rhodium and palladium, a content of rhodium being not less than 10 mass % to the entire of the noble metal catalyst, and a content of palladium is being not less than 20 mass % to the entire of the noble metal catalyst.

In accordance with a second aspect of the present invention, there is provided a gas sensor which is equipped with the gas sensor element according to the first aspect of the present invention.

In accordance with a third aspect of the present invention, there is provided a method of producing the gas sensor element according to the first aspect of the present invention. In the method of the third aspect of the present invention, a catalyst paste is printed on an outer surface of the ceramics sheet of the porous diffusion resistance layer in order to make a catalyst layer on the outer surface of the porous diffusion resistance layer.

In the catalyst layer in the gas sensor element according to the first aspect of the present invention, the content of rhodium is not less than 10 mass %, and the content of palladium is not less than 20 mass %. This structure makes it possible to provide the gas sensor element with high durability of the noble metal catalyst. That is, because rhodium has a superior thermal resistance, the presence of the rhodium of not less than 10 mass % makes it possible to prevent the noble metal catalyst from coagulating and vaporizing, and increase thermal resistance. Further, the containing of palladium of not less than 20 mass % makes it possible to increase oxidation resistance of the noble metal catalyst.

The interaction between the above two features makes it possible to suppress deterioration of the noble metal catalyst under various strict conditions such as oxidation atmosphere and reduction atmosphere. As a result, the present invention provides the gas sensor element having the catalyst layer which contains the noble metal catalyst with superior high durability.

Still further, because the gas sensor element according to the first aspect of the present invention has the catalyst layer which contains at least rhodium and palladium, it is possible to perform adequate combustion of $H_2$ gas contained in target gas to be detected. This can prevent for the gas sensor from to outputting an incorrect detection signal which is away from a true value regarding a true concentration of a specific gas contained in the target gas.

As described above, it is possible to provide the gas sensor element with superior high durability of the catalyst layer while preventing an incorrect output which is away from its true output as the detection result.

The second aspect of the present invention can provide the gas sensor equipped with the gas sensor element according to the first aspect of the present invention having the catalyst layer with high durability and preventing an incorrect detection signal which is away from its true value.

In the method according to the third aspect of the present invention, the catalyst layer is formed by printing the catalyst paste on the outer surface of the porous diffusion resistance layer. This technique to print or apply the catalyst paste on the outer surface of the porous diffusion resistance layer can easily form the catalyst layer on a desired position by a simple method. This makes it possible to easily produce the gas sensor element having the catalyst layer with superior durability and with low manufacturing cost.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Hereinafter, various embodiments of the present invention will be described with reference to the accompanying drawings. In the following description of the various embodiments, like reference characters or numerals designate like or equivalent component parts throughout the several diagrams.
Preferred Embodiments According to the Present Invention There are in general various types of gas sensor elements such as A/F sensor elements, $O_2$ sensor elements, and NOx sensor elements. The A/F sensor element is incorporated in an A/F sensor which is placed in an exhaust gas passage of an internal combustion engine such as vehicle engines. The A/F sensor is used in an exhaust gas feedback system. The $O_2$ sensor element detects a concentration of $O_2$ gas contained in an exhaust gas emitted from an internal combustion engine. The NOx sensor detects a concentration of air pollutant such as NOx. This NOx sensor is used to detect deterioration of a three-way catalyst placed in an exhaust gas passage.

There is a possibility to decrease thermal resistance capability of a catalyst layer in a gas sensor element when the content of rhodium to the entire content of noble metal catalysts is less than 10 mass %.

In addition, there is a possibility to decrease oxidation resistance capability of the catalyst layer in the gas sensor element when the content of palladium to the entire content of noble metal catalysts is less than 20 mass %.

The gas sensor (according to the second aspect of the present invention) equipped with the gas sensor element (according to the first aspect of the present invention) can be applied to various types of engines such as diesel engines, cogeneration (also combined heat and power, CHP) which is the use of a heat engine or a power station to simultaneously generate both electricity and useful heat, etc.

According to the present invention, it is preferred for the noble metal catalysts in the catalyst layer in the gas sensor element to contain platinum. This can more increase the catalyst capability of the catalyst layer by the presence of platinum. Platinum has superior catalyst capability.

It is also preferred for the combination of platinum, palladium and rhodium to have the content of 10 to 70 mass % of platinum, 20 to 80 mass % of palladium, and 10 to 15 mass % of rhodium, as shown in the third embodiment of the present invention. This combination of the noble metal catalysts makes it possible to provide a gas sensor element with superior high durability under any one of oxidation atmosphere and reduction atmosphere. Selecting a limitation to the combination in content of the noble metal catalysts can provide a gas sensor element with more superior durability under a specific atmosphere, for example, under an oxidation atmosphere or an reduction atmosphere.

According to the present invention, it is preferred that the content of rhodium in the entire noble metal catalysts is not less than 80 mass %. This makes it possible to further increase the oxidation resistance of the catalyst layer, and to have the catalyst layer with more superior durability under an oxidation atmosphere.

It is possible for the gas sensor element to adequately obtain the above superior functions such as action and effects unless having not less than 68 mass % of palladium even if the catalyst layer has a low content of platinum.

It is possible for the catalyst layer in the gas sensor element according to the present invention to have 35 to 70 mass % of platinum and 20 to 55 mass % of palladium. This makes it possible to increase oxidation resistance under an oxidation atmosphere because of having the above content of palladium as oxide which shows a high catalyst activity.

On the other hand, when the content of platinum is less than 35 mass % and the content of palladium is less than 20 mass % in a gas sensor element, there is a possibility to decrease oxidation resistance of the noble metal catalysts in the catalyst layer in the gas sensor element.

When the content of platinum is more than 70 mass %, or the content of palladium is more than 55 mass %, there is a possibility to decrease thermal resistance of the catalyst layer because of not having an adequate amount of rhodium in the catalyst layer.

It is possible for the catalyst layer in the gas sensor element a according to the present invention to have not less than 50 mass % of noble metal catalysts to the entire content of the catalyst layer. This makes it possible to provide the gas sensor element with superior catalyst capability after durability test because of having an adequate amount of the noble metal catalysts in the catalyst layer.

On the other hand, when the catalyst layer has less than 50 mass % of noble metal catalysts to the entire content of the catalyst layer, there is a possibility for a gas sensor element to decrease its catalyst capability.

It is preferable to apply the gas sensor equipped with the gas sensor element according to the present invention to various types of engines such as direct injection engines, turbo engines, and compressed natural gas engines, where the direct injection engine directly injects fuel into combustion chambers, the turbo engine is equipped with an exhaust gas turbine supercharger, and the compressed natural gas engine uses compressed natural gas.

This makes it possible to show the superior features of the gas sensor element previously described in those engines. That is, because those engines discharge an exhaust gas, in particular, which contains $H_2$ gas, the use of the gas sensor equipped with the has sensor element according to the present invention in those engines can show its specific features previously described and can prevent any incorrect detection which is away from its correct detection.

A description will be given of various embodiments of the present invention. However, the concept of the present invention is not limited by the following embodiments.

First Embodiment

A description will now be given of a gas sensor element, a gas sensor equipped with the gas sensor element, and a method of producing the gas sensor element according to the first embodiment of the present invention with reference to FIG. 1 to FIG. 4, and FIG. 7.

Figure 1:
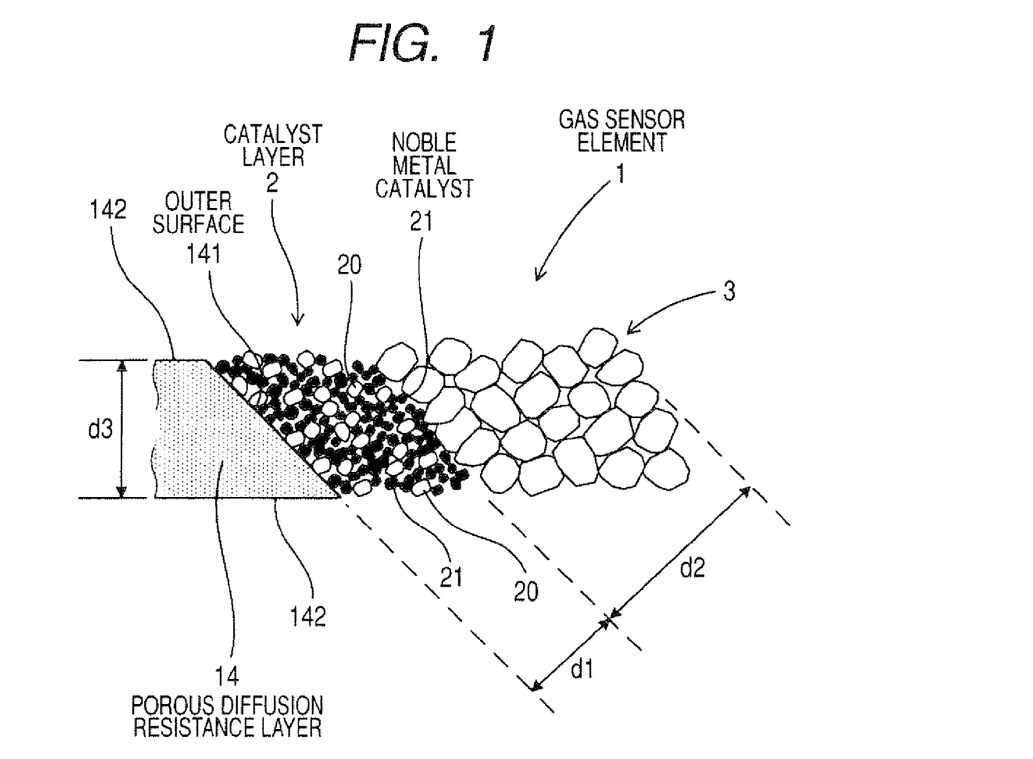
FIG. 1 is a cross section mainly showing a catalyst layer in a gas sensor element according to a first embodiment of the present invention.
Figure 2:
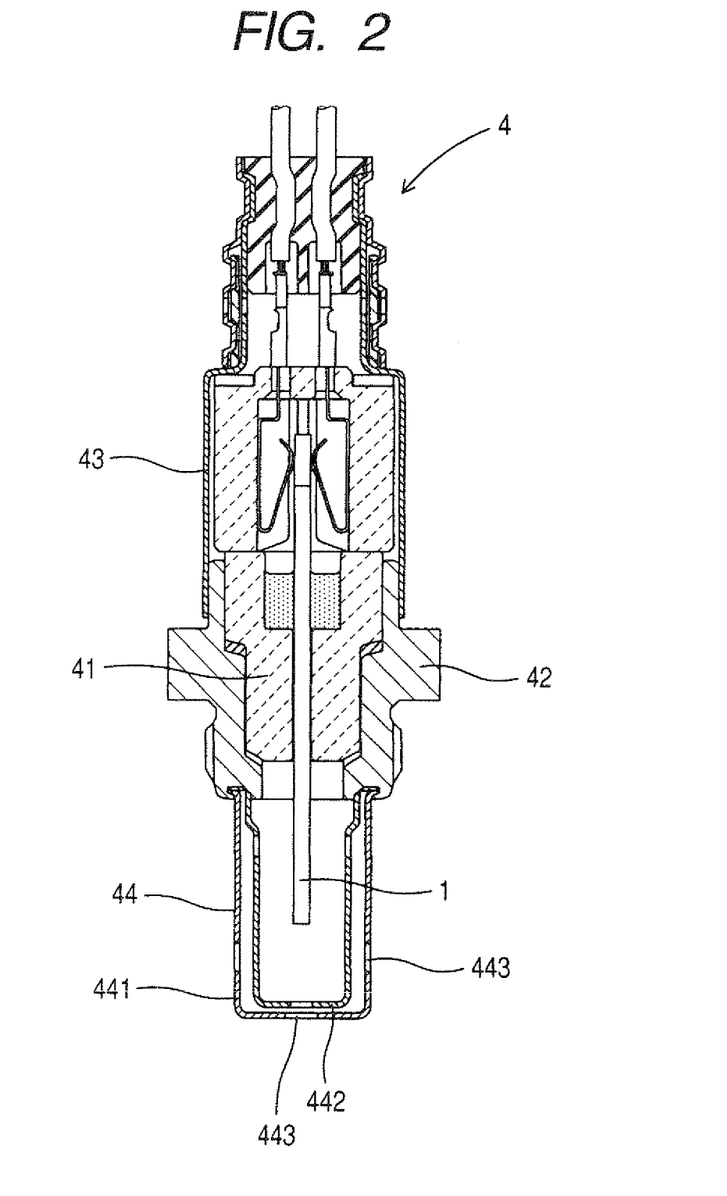
FIG. 2 is a cross section showing the gas sensor equipped with the gas sensor element shown in FIG. 1 along its longitudinal direction.
Figure 3:
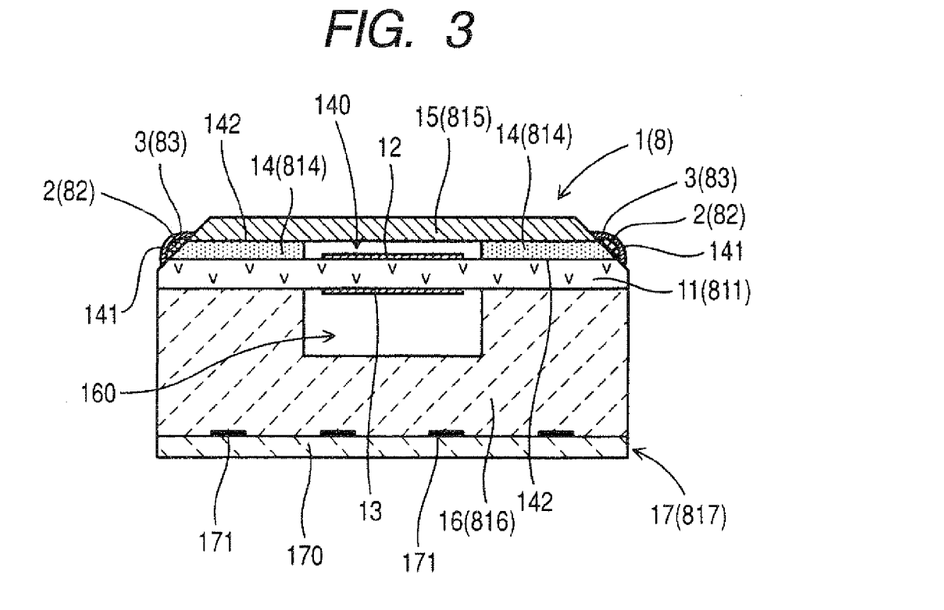
FIG. 3 is a cross section showing the gas sensor element in a direction which is perpendicular to the axial direction of the gas sensor element according to the first embodiment of the present invention.

FIG. 1 is a cross section showing a catalyst layer 2 in the gas sensor element 1 according to the first embodiment of the present invention. FIG. 2 is a cross section showing the gas sensor element 1 along its longitudinal direction according to the first embodiment. FIG. 3 is a cross section showing the gas sensor element 1 in a direction which is perpendicular to the axial direction of the gas sensor element according to the first embodiment.

As shown in FIG. 3, the gas sensor 4 is equipped with the gas sensor element 1. The gas sensor element 1 according to the first embodiment is comprised of a solid electrolyte 11, a target gas electrode 12, a reference gas electrode 13, a porous diffusion resistance layer 14, and the catalyst layer 2. The solid electrolyte 11 has an oxygen ion conductivity. The target gas electrode 12 is formed on one surface of the solid electrolyte 11. The reference gas electrode 13 is farmed on the other surface of the solid electrolyte 11. As shown in FIG. 3, the porous diffusion resistance layer 14 surrounds the target gas electrode 12. Through the porous diffusion resistance layer 14, the target gas to be detected passes and reaches the target gas electrode.

The gas sensor element 1 has the catalyst layer 2 as shown in FIG. 1. The catalyst layer 2 is formed on the outer surface 141 of the porous diffusion resistance layer 14 through which the target gas is introduced into the inside of the gas sensor element 1. The catalyst layer 2 contains noble metal catalysts 21.

The noble metal catalysts 21 in the gas sensor element 1 contains at least rhodium (Rh) and palladium (Pd).

The content of rhodium to the entire content of the noble metal catalysts 21 is not less than 10 mass %, and the content of palladium to the entire content of the noble metal catalysts 21 is not less than 20 mass %.

In the first embodiment, the noble metal catalysts 21 in the catalyst layer 2 is composed of 45 mass % of platinum, 45 mass % of palladium, and 10 mass % of rhodium.

As shown in FIG. 2, the gas sensor 4 further has an insulator 41 and a housing 42, an atmosphere cover case 43, and an element cover case 44. The insulator 41 accommodates the gas sensor element 1 and supports it in the inside thereof. The housing 42 accommodates the insulator 41 and supports it in the inside thereof. The atmosphere cover case 43 is caulked to maintain and fix the housing 42 to the inner diameter direction at a base side of the housing 42. The element cover case 44 is placed at the front end part of the housing 42 to protect the gas sensor element 1 from damage to be applied from outside.

The element cover case 44 is a multiple structure cover case which is composed of an outer cover case 441 and an inner cover case 442. The outer cover case 441 and the inner cover case 442 have introduction through holes 443 which are formed at the side surface and the bottom surface thereof.

It is possible to apply the gas sensor equipped with the gas sensor element 1 according to the first embodiment to various types of engines such as direct injection engines, turbo engines equipped with an exhaust gas turbine supercharger, and compressed natural gas engines.

Figure 4:
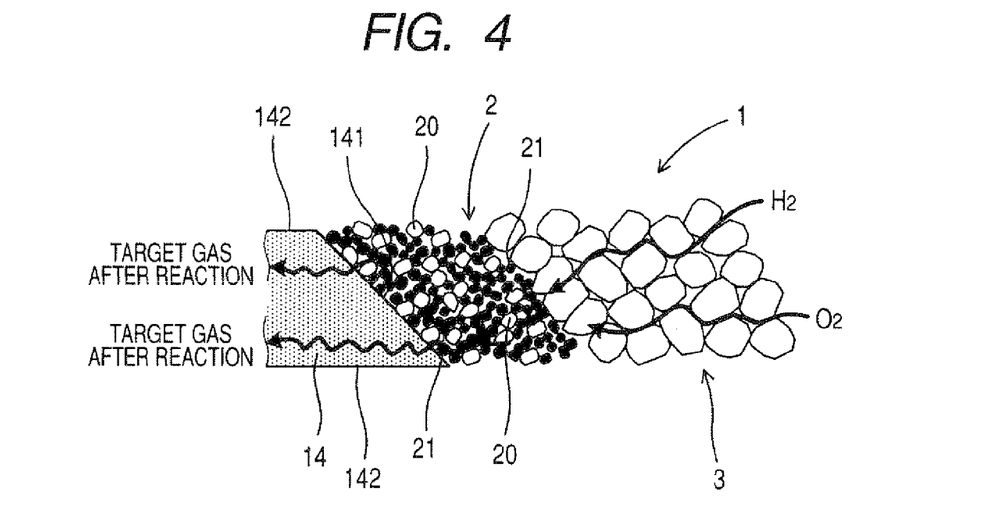
FIG. 4 is a view to explain an introduction passage of a target gas which is introduced through the catalyst layer into the inside of the gas sensor element according to the first embodiment of the present invention.

As shown in FIG. 1, FIG. 3, and FIG. 4, the gas sensor element 1 is comprised of the solid electrolyte 11, the target gas electrode 12, the reference gas electrode 13, the porous diffusion resistance layer 14, the catalyst layer 2, a trap layer 3, and a shielding layer 15. The outer surface of the catalyst layer 2 is covered with the trap layer 3. This shielding layer 15 covers the upper surface of the porous diffusion resistance layer 14, as shown in FIG. 3, that is, covers the opposite surface to the surface of the porous insulation layer 14. The porous insulation layer 14 faces the surface of the solid electrolyte 11.

Further, as shown in FIG. 3, the gas sensor element 1 according to the first embodiment has a reference gas chamber forming layer 16 in order to form a reference gas chamber 160 at the reference gas electrode 13 side in the reference gas chamber forming layer 16. A reference gas is introduced into the inside of the reference gas chamber 160. As shown in FIG. 3, a heating layer 17, the reference gas chamber forming layer 16, the solid electrolyte 11, the porous diffusion resistance layer 14, and the shielding layer 15 are stacked to make a lamination body. This heating layer 17 contains heating substrate 170 equipped with a plurality of heating parts 171 therein. When receiving an electric power, the heating parts 171 generate heat energy.

A description will now be given of the gas sensor element 1 according to the first embodiment in more detail.

The catalyst layer 2 is made of alumina particles ($Al_2O_3$) 20 and noble metal catalysts 21. The alumina particles 20 have an average particle size of 1.5 μm, for example. The compositional structure and feature of the noble metal catalysts 21 in the catalyst layer 2 will be explained later in detail.

As shown in FIG. 1, the catalyst layer 2 has a thickness d2 within a range of 3 to 20 μm. In the first embodiment, the thickness d1 of the catalyst layer 2 is 10 μm.

The catalyst layer 2 contains the noble metal catalysts 21 having an average particle size of 0.5 μm, for example. The noble metal catalysts 21 are composed of 10 mass % of rhodium, 45 mass % of palladium, and 45 mass % of platinum, for example.

The content of the noble metal catalysts 21 is within a range of 50 to 90 mass % to the entire content of the catalyst layer 2. It is also possible for the noble metal catalysts to have the content of 100 mass % in the catalyst layer 2.

In the gas sensor element 1 according to the first embodiment, the noble metal catalysts 21 has the content of 80 mass % to the entire content of the catalyst layer 2 in order to keep the catalyst capability and to maintain its durability. In other words, the gas sensor element 1 according to the first embodiment has the catalyst layer 2 which is made of material composed of the alumina particles 20 and the noble metal catalysts 21, not but that a small amount of fine noble metal catalysts is supported on the alumina particles in the catalyst layer.

$H_2$ gas contained in the target gas is fired in the catalyst layer 2 which will be explained later in detail.

The trap layer 3 is made of alumina having an average particle size of 20 μm, for example. As shown in FIG. 1, the trap layer 3 has a thickness d2 within a range of 10 to 600 μm, for example. In the first embodiment, the trap layer 3 has the thickness d2 of 200 μm. This trap layer 3 captures CO gas, NO gas, and $CH_4$ gas which will be explained later.

As shown in FIG. 1, FIG. 3, and FIG. 4, the catalyst layer 2 is formed on the outer surface 141 of the porous diffusion resistance layer 14 through which the target gas is introduced into the inside of the gas sensor element 1. That is, one outer surface 142 of the porous diffusion resistance layer 14, through which no target gas is introduced, is covered with a dense shielding layer 15. Further, the other outer surface of the porous diffusion resistance layer 14, through which no target gas is introduced, is formed on the solid electrolyte 11. As shown in FIG. 3, the trap layer 3 is formed at the outer surface of the catalyst layer 2.

The porous diffusion resistance layer 14 is made of alumina, for example. Further, the average particle size of alumina forming the porous diffusion resistance layer 14 is 1.5 μm, for example, and a porosity of the porous diffusion resistance layer 14 is within a range of 10 to 60%. Further, as shown in FIG. 1, the porous diffusion resistance layer 14 has a thickness d2 of 10 μm, for example.

Next, a description will now be given of a method of producing the gas sensor element 1 according to the first embodiment of the present invention with reference to FIG. 3 and FIG. 7.

Figure 7:
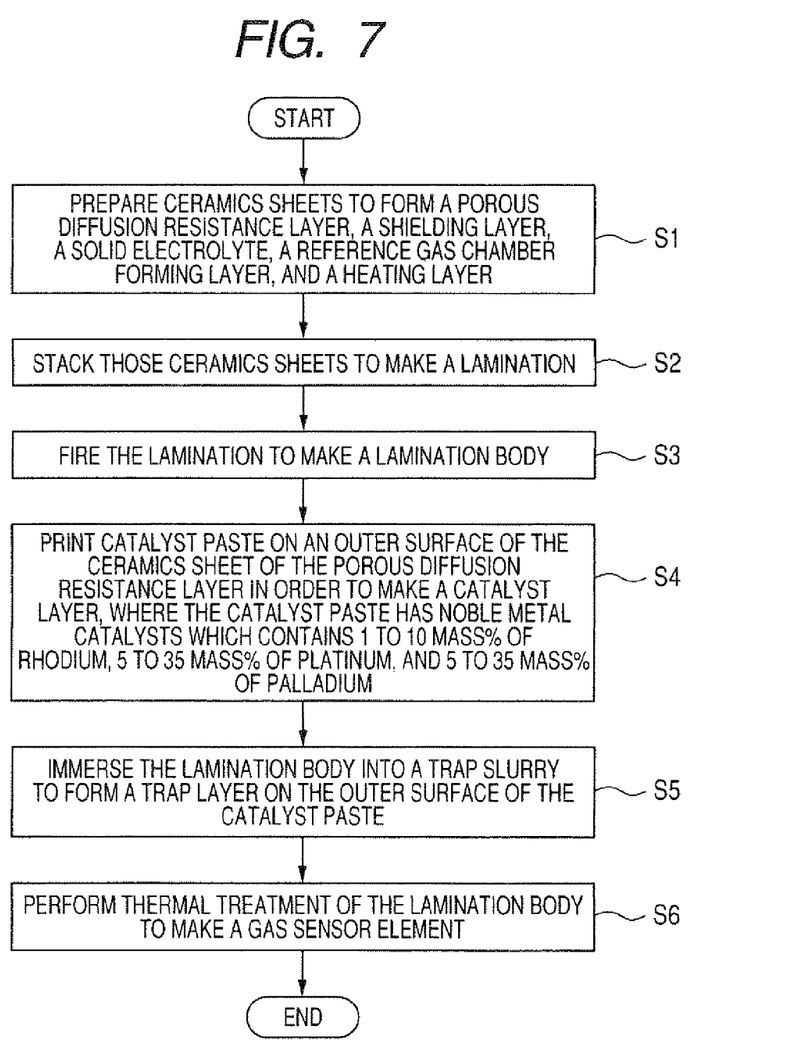
FIG. 7 is a flow chart showing a method of producing the gas sensor element according to the present invention.

FIG. 7 is a flow chart showing the method of producing the gas sensor element 1 according to the first embodiment of the present invention.

In step S1, ceramics sheets 814, 815, 811, 816, and 817 are prepared in order to form the porous diffusion resistance layer 14, the shielding layer 15, the solid electrolyte 11, the reference gas chamber forming layer 16, and the heating layer 17, respectively.

Next, the ceramics sheets 817, 816, 811, 814, and 815 are stacked to make a lamination (step S2). The lamination is then fired to make a lamination body 8 (step S3).

After step S3, a catalyst paste 82 is printed on an outer surface 141 of the ceramics sheet 814 of the porous diffusion resistance layer 14 in order to make the catalyst layer 2 (step S4). The catalyst paste 82 has noble metal catalysts which contain 1 to 10 mass % of rhodium, 5 to 35 mass % of platinum, and 5 to 35 mass % of palladium.

Next, the lamination body 8 is immersed into a trap slurry to form the trap layer 3 on the outer surface of the catalyst paste 82 (step S5).

After this process, a thermal treatment of the lamination body 8 is performed to make the gas sensor element 1 according to the first embodiment of the present invention (step S6).

Next, a description will now be given of the functions of the catalyst layer 2 and the trap layer 3 with reference to FIG. 4.

FIG. 4 is a view to explain an introduction passage of a target gas to be detected into the inside of the gas sensor element 1 according to the first embodiment.

For example, the target gas emitted from an internal combustion engine contains $H_2$ gas, $O_2$ gas, CO gas, NO gas, and $CH_4$ gas. The target gas to be detected is introduced into the inside of the gas sensor element 1 through the introduction holes 443 which are formed in the element cover case 44.

Next, the target gas passes through the trap layer 3, the catalyst layer 2, and the porous diffusion resistance layer 14, and finally reaches the target gas electrode 12. In particular, because $H_2$ gas has a high diffusion speed in the porous diffusion resistance layer 14, $H_2$ gas reaches the target gas electrode 12 first, rather than the remaining gases. This causes a possibility for the gas sensor element to cause an incorrect detection which is away from its true detection regarding a concentration of a specific gas contained in the target.

In the gas sensor element 1 according to the first embodiment of the present invention, the catalyst layer 2 has the noble metal catalysts 21 which contain rhodium, palladium, and platinum. Because this structure of the catalyst layer 2 adequately performs the combustion of $H_2$ gas contained in the target gas, it is possible for the gas sensor element 1 according to the first embodiment to output a correct detection signal, not to output any incorrect detection signal.

A description will now be given of actions and effects of the gas sensor element 1 according to the first embodiment of the present invention.

In the gas sensor element 1 according to the first embodiment, the catalyst layer 2 contains not less than 10 mass % of Rhodium, not less than 20 mass % of palladium. This structure provides the gas sensor element 1 having the catalyst layer 2 which contains the noble metal catalyst 21 with superior durability In general, because rhodium has superior durability, containing a specific amount of rhodium described above can prevent the noble metal catalysts 21 from coagulating and vaporizing, and increase thermal resistance. Further, containing the above specific amount of palladium can increase oxidation resistance of the catalyst layer 21.

The interaction between the above two features such as one increasing the thermal resistance and the other increasing the oxidation resistance can suppress deterioration of the noble metal catalyst 21 under various strict conditions such as under an oxidation atmosphere and reduction atmosphere. As a result, it is possible to provide the gas sensor element 1 having the catalyst layer 2 containing the noble metal catalysts 21 with superior durability.

Because the gas sensor element 1 according to the first embodiment has the catalyst layer 2 which contains at least rhodium and palladium, it is possible to perform adequate combustion of $H_2$ gas contained in the target gas to be detected. This can prevent for the gas sensor element 1 to output an incorrect detection signal which is away from a true detection signal regarding a true concentration of a specific gas contained in the target gas.

It is possible for the structure of the gas sensor element 1 to further increase the performance of catalyst in the catalyst layer 2 by the catalyst function of platinum because the catalyst layer 2 contains platinum as one of the noble metal catalysts 21.

Still further, the content of the noble metal catalyst 21 is within a range of 50 to 90 mass % to the entire of the catalyst layer 2. This can adequately keep an accuracy of stoichiometry after durability test.

The method of producing the gas sensor element 1 according to the first embodiment of the present invention uses the technique to form the catalyst layer 2 by printing the catalyst paste on the outer surface 141 of the porous diffusion resistance layer 14. This technique to print or apply the catalyst paste on the outer surface of the porous diffusion resistance layer 14 can easily form the catalyst layer 2 on a desired position. This makes it possible to easily produce the gas sensor element 1 having the catalyst layer 2 with superior durability and with low manufacturing cost.

The gas sensor 4 equipped with the gas sensor element 1 is mounted on various types of engines such as direct injection engines capable of directly injecting fuel into a combustion chamber, turbo engines equipped with an exhaust gas turbine supercharger, and compressed natural gas engines using compressed natural gas as fuel. Accordingly, it is possible for the gas sensor 4 to show the superior features of the gas sensor element 1 according to the present invention. That is, the above engines discharge an exhaust gas which usually contains $H_2$ gas. Mounting the gas sensor 4 equipped with the gas sensor element 1 according to the present invention on those engines can remarkably show the actions and effects of the present invention.

As described above, the present invention provides the gas sensor element 1 and the gas sensor 4 having the catalyst layer 2 which contains the noble metal catalysts 21 with high durability capable of avoiding outputting of an incorrect detection signal which is away from its true detection signal.

Second Embodiment

A description will be given of a second embodiment of the present invention where the stoichiometry accuracy of the gas sensor element is detected after durability test while changing the content of platinum (Pt), palladium (Pd), and rhodium (Rh) in the noble metal catalysts 21 in the catalyst layer 2.

The experimental test according to the second embodiment prepared the following samples of the gas sensor elements in which the content of platinum in the noble metal catalysts 21 is changed within a range of 10 to 100 mass %, palladium within a range of 0 to 80 mass %, and rhodium within a range of 0 to 10 mass %.

Those samples were fired at 950° C. over 200 hours under an oxidation atmosphere.

After completion of the firing step, the second embodiment detects a difference between an actual output (as a detection signal) and a theoretical value (as an output value) of the samples under stoichiometry atmosphere of a same chemical equivalent of oxidation gas and reduction gas.

In addition, the same durability test for the experimental samples was performed at 950° C. over 200 hours under reduction atmosphere containing 100% of $N_2$ gas.

Next, a description will now be given of a judging standard of the stoichiometry accuracy after durability test.

The experimental results of the second embodiment are shown in the following Table 1, where "⊚" designates the difference within less than 5%, "○" denotes the difference within a range of not less than 5% and less than 20%, and "X" indicates the difference within not less than 20%.

TABLE 1

| Sample | Content (mass %) of Noble metal catalyst | | | Judgment results of sensor accuracy after durability test under oxidation atmosphere | Judgment results of sensor accuracy after durability test under reduction atmosphere |
|---|---|---|---|---|---|
| | Pt | Rh | Pd | | |
| 1 | 100 | 0 | 0 | X | X |
| 2 | 95 | 5 | 0 | X | X |
| 3 | 90 | 10 | 0 | X | X |
| 4 | 90 | 0 | 10 | X | X |
| 5 | 85 | 0 | 15 | X | X |
| 6 | 80 | 10 | 10 | X | X |
| 7 | 80 | 5 | 15 | X | X |
| 8 | 80 | 0 | 20 | X | X |
| 9 | 70 | 0 | 30 | X | X |
| 10 | 70 | 10 | 20 | ○ | ⊚ |
| 11 | 60 | 10 | 30 | ○ | ⊚ |
| 12 | 55 | 10 | 35 | ○ | ⊚ |
| 13 | 50 | 10 | 40 | ○ | ⊚ |
| 14 | 45 | 10 | 45 | ○ | ⊚ |
| 15 | 42.5 | 15 | 42.5 | ○ | ⊚ |
| 16 | 40 | 10 | 50 | ○ | ⊚ |
| 17 | 35 | 10 | 55 | ○ | ⊚ |
| 18 | 30 | 10 | 60 | ○ | ○ |
| 19 | 22 | 10 | 68 | ⊚ | ○ |
| 20 | 20 | 10 | 70 | ⊚ | ○ |
| 21 | 10 | 10 | 80 | ⊚ | ○ |
| 22 | 0 | 10 | 90 | ○ | ○ |

As can be understood from the experimental results shown in Table 1, the samples 10 to 22 having the catalyst layer which contains not less than 10 mass % of rhodium, and not less than 20 mass % of palladium have a good judgment result designated by "⊚" or "○". Accordingly, those samples 10 to 22 have superior stoichiometry accuracy (or superior sensor accuracy) after durability test.

In more detail, as can be understood from the experimental results shown in Table 1, when the samples having the catalyst layer which contains 0 to 70 mass % of platinum, 10 to 15 mass % of rhodium, and 20 to 90 mass % of palladium have superior stoichiometry accuracy, that is, have superior accuracy after durability test under any one of oxidation atmosphere and reduction atmosphere.

In particular, the samples 19 to 22 having the catalyst layer in which the content of palladium to the entire content of the noble metal catalyst is not less than 68 mass % have the judgment result of the stoichiometry accuracy designated by "⊚" under an oxidation atmosphere. This means that those samples 19 to 22 have a very small difference between the output thereof and the true output under an oxidation atmosphere.

On the other hand, the samples 10 to 17 having the catalyst layer which contains 35 to 70 mass % of platinum, 10 mass % of rhodium, and 20 to 55 mass % of palladium to the entire content of the noble metal catalyst have a good judgment result of the stoichiometry accuracy after durability test designated by "⊚" under reduction atmosphere. This means that those samples 10 to 17 have a very small difference between the output thereof and the true output under reduction atmosphere.

On the other hand, the samples 1 to 9 having the catalyst layer which contains less than 10 mass % of rhodium or 20 mass % of palladium have a bad good judgment result of the stoichiometry accuracy after durability test designated by "X" under any one of oxidation atmosphere and reduction atmosphere. This means that those samples 1 to 9 have bad stoichiometry accuracy after durability test.

As described above, it can be understood for the gas sensor element to have good stoichiometry accuracy under various controlled environment when it has the catalyst layer which contains 10 mass % of rhodium and 20 mass % of palladium to the entire content of the noble metal catalysts. Accordingly, it is possible to provide the gas sensor element having the catalyst layer with high durability when the content of palladium and platinum is changed according to various strict conditions such as oxidation atmosphere, and reduction atmosphere.

Third Embodiment

A description will be given of a third embodiment of the present invention where the stoichiometry accuracy (or sensor accuracy) of the gas sensor element is detected after durability test while changing the content of the noble metal catalysts in the catalyst layer.

The third embodiment uses various types of samples as the gas sensor element where the content of the noble metal catalysts to the entire content of the catalyst layer was changed. In particular, each of the samples has the noble metal catalysts which contains 45 mass % of platinum, 45 mass % of palladium, and 10 mass % of rhodium. Like the second embodiment, in the third embodiment, the durability test was performed to each of those samples.

As a result, Table 2 shows the experimental results of the third embodiment, where "⊙" designates the difference (from the true value) within less than 5%, "○" denotes the difference within a range of not less than 5% and less than 20%, "Δ" denotes the difference within a range of not less than 20% and less than 50%, and "X" indicates the difference within not less than 50%.

TABLE 2

| Content (mass %) of noble metal catalyst in catalyst layer | Judgment results of sensor accuracy after durability test |
| --- | --- |
| 1 | X |
| 5 | X |
| 20 | Δ |
| 50 | ○ |
| 80 | ⊙ |
| 90 | ⊙ |
| 100 | ⊙ |

As can be understood from Table 2, the samples having the catalyst layer which contains not less than 50 mass % of the noble metal catalysts designated by "↑" or "○" have a good stoichiometry accuracy after durability test.

In particular, the sample having the catalyst layer which contains not less than 80 mass % of the noble metal catalysts designated by "⊙" have a superior stoichiometry accuracy after durability test.

On the other hand, the samples having the catalyst layer which contains less than 50 mass % of the noble metal catalysts designated by "Δ" or "X" have a bad stoichiometry accuracy after durability test.

Accordingly, it is preferable for the gas sensor element to have the catalyst layer which contains not less than 50 mass % of the noble metal catalysts, more preferable to have the catalyst layer which contains noble metal catalyst within a range of 80 to 100 mass %.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A gas sensor element comprising:
a solid electrolyte with an oxygen ion conductivity;
a target gas electrode formed on one surface of the solid electrolyte, and a reference gas electrode formed on the other surface of the solid electrolyte;
a porous diffusion resistance layer surrounding the target gas electrode, through which the target gas passes and reach the target gas electrode; and
a catalyst layer formed on an outer surface of the porous diffusion resistance layer, through which the target gas is introduced into the inside of the gas sensor element, the catalyst layer containing noble metal catalysts, the noble metal catalysts consisting of rhodium, palladium, and platinum,
when an entirety of the noble metal catalysts is 100 mass %, a content of rhodium being within a range of 10 to 15 mass % to the entire of the noble metal catalysts, a content of palladium is being within a range of 20 to 55 mass % to the entire of the noble metal catalysts, a content of platinum is within a range of 35 to 70 mass % to the entire of the noble metal catalysts, and
the content of the noble metal catalysts in the catalyst layer is not less than 50 mass % to the entire of the catalyst layer.

2. A gas sensor equipped with the gas sensor element therein according to claim 1 and capable of detecting a concentration of a specific gas contained in the target gas.

3. The gas sensor according to claim 2 to be applied to one of direct injection engines to directly inject fuel into combustion chambers, turbo engines equipped with an exhaust gas turbine supercharger, and compressed natural gas engines using compressed natural gas.

4. The gas sensor element according to claim 1, wherein
the content of rhodium is 10 mass % to the entire of the noble metal catalysts,
the content of palladium is 20 mass % to the entire of the noble metal catalysts, and
the content of platinum is 70 mass % to the entire of the noble metal catalysts.

5. The gas sensor element according to claim 1, wherein
the content of rhodium is 10 mass % to the entire of the noble metal catalysts,
the content of palladium is 30 mass % to the entire of the noble metal catalysts, and
the content of platinum is 60 mass % to the entire of the noble metal catalysts.

6. The gas sensor element according to claim 1, wherein
the content of rhodium is 10 mass % to the entire of the noble metal catalysts,
the content of palladium is 35 mass % to the entire of the noble metal catalysts, and
the content of platinum is 55 mass % to the entire of the noble metal catalysts.

7. The gas sensor element according to claim 1, wherein
the content of rhodium is 10 mass % to the entire of the noble metal catalysts,
the content of palladium is 40 mass % to the entire of the noble metal catalysts, and
the content of platinum is 50 mass % to the entire of the noble metal catalysts.

8. The gas sensor element according to claim 1, wherein
the content of rhodium is 10 mass % to the entire of the noble metal catalysts,
the content of palladium is 45 mass % to the entire of the noble metal catalysts, and
the content of platinum is 45 mass % to the entire of the noble metal catalysts.

9. The gas sensor element according to claim 1, wherein
the content of rhodium is 15 mass % to the entire of the noble metal catalysts,
the content of palladium is 42.5 mass % to the entire of the noble metal catalysts, and
the content of platinum is 42.5 mass % to the entire of the noble metal catalysts.

10. The gas sensor element according to claim 1, wherein
the content of rhodium is 10 mass % to the entire of the noble metal catalysts,
the content of palladium is 50 mass % to the entire of the noble metal catalysts, and
the content of platinum is 40 mass % to the entire of the noble metal catalysts.

11. The gas sensor element according to claim 1, wherein
the content of rhodium is 10 mass % to the entire of the noble metal catalysts,
the content of palladium is 55 mass % to the entire of the noble metal catalysts, and
the content of platinum is 35 mass % to the entire of the noble metal catalysts.

\* \* \* \* \*